United States Patent [19]

Moriuchi et al.

[11] Patent Number: 5,053,507

[45] Date of Patent: Oct. 1, 1991

[54] OPTICALLY ACTIVE PYRIMIDINES DERIVATIVES

[75] Inventors: Fumio Moriuchi, Suita; Hiroshi Yano; Kazushige Kajita, both of Osaka, all of Japan

[73] Assignee: Arakawa Kagaku Kogyo Kabushiki Kaisha, Osaka, Japan

[21] Appl. No.: 497,057

[22] Filed: Mar. 21, 1990

[30] Foreign Application Priority Data

Apr. 1, 1989 [JP] Japan ................................. 1-82700
Nov. 6, 1989 [JP] Japan ................................. 1-289749

[51] Int. Cl.$^5$ ................. C07D 239/02; C07D 309/06; C09K 19/52
[52] U.S. Cl. ................................. 544/334; 544/335; 549/372; 549/373; 549/375; 549/423; 549/420; 560/61; 252/299.01; 252/299.2; 568/608
[58] Field of Search .............................. 544/334, 335

[56] References Cited

U.S. PATENT DOCUMENTS 4,904,409  2/1990  Miyazawa et al. ................. 544/335

FOREIGN PATENT DOCUMENTS

0288297A2  10/1988  European Pat. Off. .

OTHER PUBLICATIONS

Chemical Abstracts, vol. 105 (1986), p. 598, No. 97086e.
Gerald Kirchner et al, "Resolution of Racemic Mixtures via Lapase Catalysis in Organic Solvents", *J. Am. Chem. Soc.* 1985, 107, 7072-7076.
Aleksey Zaks et al, "Enzyme-catalyzed processes in organic solvents", *Proc. Natl. Acad. Sci. U.S.A.*, vol. 82, pp. 3192-3196, May 1985.
Alexander M. Klibanov, "Enzymes that work in organic solvents", *CHEMTECH*, pp. 354-359, Jun. 1986.

*Primary Examiner*—Johann Richter
*Attorney, Agent, or Firm*—Armstrong, Nikaido, Marmelstein, Kubovcik & Murray

[57] ABSTRACT

Optical active compounds of the formula (1), (2), (3) and (4):

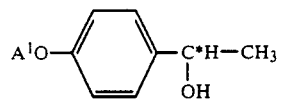

(1)

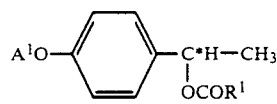

(2)

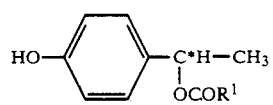

(3)

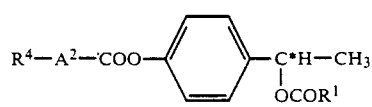

(4)

The compounds (1), (2) and (3) are useful as raw materials of chiral dopants to be added for forming liquid crystal compositions, medicines or agricultural chemicals, and the compound (4) is useful as chiral dopants to be added for forming liquid crystal compositions.

1 Claim, No Drawings

OPTICALLY ACTIVE PYRIMIDINES DERIVATIVES

BACKGROUND OF THE INVENTION

The present invention relates to optically active compounds and preparation processes thereof. More particularly, the present invention relates to optically active compounds useful as raw materials of chiral dopants to be added for forming liquid crystal compositions, raw materials of medicines or agricultural chemicals and a preparation process thereof; and an optically active compound useful as chiral dopants (additives) for forming ferroelectric liquid crystal compositions, a preparation process thereof.

The liquid crystal display cell or device most widely used at present is a twisted nematic (TN) mode display cell or device, but it has the defect that the response time is slow as compared with display systems of light emitting type such as electroluminescence display and plasma display. In order to improve the defect, various studies have been made.

For instance, a display system using ferroelectric liquid crystals is proposed as a liquid crystal display utilizing a different principle from the TN mode display by N. A. Clark et al. in Applied Physics Letters, Vol. 36, 899(1980). This display system utilizes the chiral smectic C phase of ferroelectric liquid crystals. It is superior to the TN mode display in high speed responsibility and the like. The high speed responsibility would also make a large capacity display possible. Accordingly, as a ferroelectric liquid crystal display material there has been demanded a ferroelectric liquid crystal compound capable of exhibiting the chiral smectic C phase and having a large spontaneous polarization (Ps). However, no satisfactory ferroelectric liquid crystal has been provided.

It is known that a liquid crystal composition having high speed responsibility can be obtained by adding an optically active compound, which does not exhibit the mesophase in itself, to smectic liquid crystals or nematic liquid crystals The properties of the liquid crystal composition greatly vary depending on the kinds of the used optically active compounds and the liquid crystal monomers, the ratio of the compound to the monomer in the composition, the compatibility of the compound with the monomer, and the like. So, the scope of investigation for ferroelectric liquid crystal materials is further widen (cf. L. A. Bresner et al, Molecular Crystals and Liquid Crystals, Vol. 89, page 327, 1982). However, in general, it is difficult to obtain optically active compounds, excepting amino acids, organic acids and saccharides which are easily available by microbial fermentation or as natural products. In particular, there has not been accomplished a technique for producing optically active compounds suitable as an additive for forming ferroelectric liquid crystal compositions by adding to smectic liquid crystals or nematic liquid crystals.

That is, when optically active compounds are prepared by biochemical method or organic chemical method, these methods are of narrow application and have following defects.

For instance, according to an asymmetric synthesis utilizing a baker's yeast or dehydrogenase as one of the biochemical methods, it tends to remarkably lower a yield or an optical purity of the desired product depending on a solubility of a used substrate to water. The method is difficult to apply to water-insoluble compounds.

Also, according to an asymmetric transesterification reaction wherein tributyrin and a secondary alcohol are conducted transesterification in an organic solvent, using lipase, as an another one of the biochemical methods, the reaction rate is very slow, and moreover since the obtained optically active compound is restricted to butyl esters, further some steps are required for obtaining a desired compound.

On the other hand, according to the organic chemical methods, there are many cases that the optical purity and the chemical yield are low depending on a used substrate and the obtained optically active compound is restricted to a low molecular weight compound. Therefore, according to the method, it is difficult to obtain optically active compounds utilizable as additives to be added to the smectic liquid crystals or the nematic liquid crystals to form liquid crystal compositions, or raw materials of the additives.

It is a primary object of the present invention to provide optically active compounds which are particularly useful as raw materials of an optically active compound having high compatibility with known smectic liquid crystals or nematic liquid crystals and capable of producing a liquid crystal composition having a high Ps value when added to the smectic liquid crystals or the nematic liquid crystals, the optically reactive compound being easily produced from the raw material.

A further object of the present invention is to provide a process for preparing the above-mentioned optically active compounds.

Another object of the present invention is to provide an optically active compound having a high compatibility with known smectic liquid crystals or nematic liquid crystals and capable of producing a liquid crystal composition having a high Ps value when added to the smectic liquid crystals or the nematic liquid crystals.

A still another object of the present invention is to provide a process for easily preparing the above-mentioned optically active compound.

These and other objects of the present invention will become apparent from the description hereinafter.

SUMMARY OF THE INVENTION

In accordance with the present invention, there are provided an optically active compound of the formula (1):

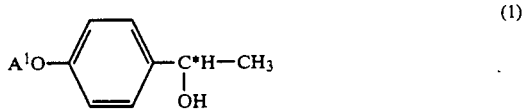

(1)

wherein $A^1$ is tetrahydro-2-pyranyl group or 1-ethoxyethyl group;
an optically active compound of the formula (2):

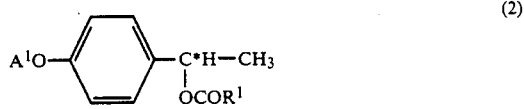

(2)

wherein $R^1$ is an alkyl group having 1 to 15 carbon atoms and $A^1$ is tetrahydro-2-pyranyl group or 1-ethoxyethyl group; and an optically active compound of the formula (3):

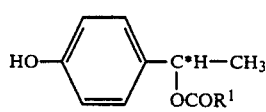
 (3)

wherein $R^1$ is an alkyl group having 1 to 15 carbon atoms.

Also, the present invention provides a process for preparing the optically active compounds (1) and (2) which comprises:

subjecting a racemic alcohol of the formula (5):

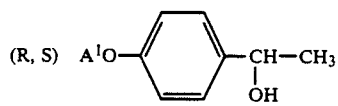
 (5)

wherein $A^1$ is as defined above, to esterification with an ester of a fatty acid having 2 to 16 carbon atoms and 2,2,2-trichloroethanol or a vinyl ester of a fatty acid of the formula (6):

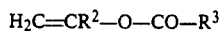
 (6)

in which $R^2$ is hydrogen atom or methyl group and $R^3$ is an alkyl group having 1 to 8 carbon atoms, in an organic solvent in the presence of an enzyme having an esterase activity to convert only the R-form of the racemic alcohol (5) into the ester, and separating the unreacted S-form of the racemic alcohol (5) from the reaction mixture.

In another aspect of the present invention, there is provided an optically active compound of the formula (4):

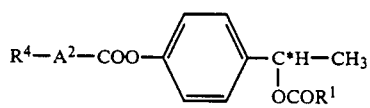
 (4)

wherein $R^1$ is an alkyl group having 1 to 15 carbon atoms, $R^4$ is an alkyl or alkyloxy group having 1 to 15 carbon atoms and $A^2$ is

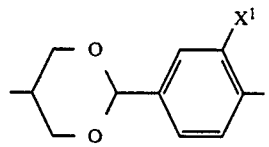

in which $X^1$ is hydrogen atom, a halogen atom or cyano group, or

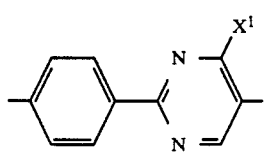

in which $X^1$ is as defined above.

Further, the present invention provides a process for preparing the optically active compound of the formula (4) which comprises subjecting a compound of the formula (7):

$$R^4-A^2-COOH \qquad (7)$$

wherein $R^4$ and $A^2$ are as defined above, to esterification with an optically active compound of the formula (3):

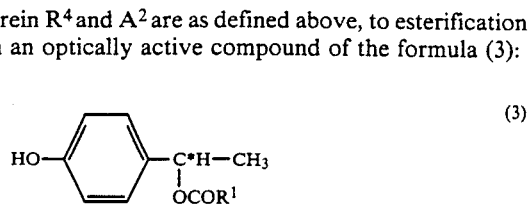
 (3)

wherein $R^1$ is as defined above.

DETAILED DESCRIPTION

In the present invention, there are provided an optically active compound of the formula (1):

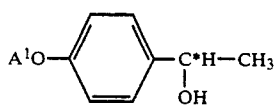
 (1)

an optically active compound of the formula (2):

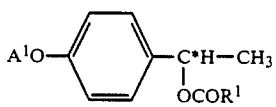
 (2)

and an optically active compound (a fatty acid ester of 1-(p-hydroxyphenylethanol) of the formula (3):

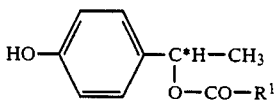
 (3)

In the instant specification, an R-form of an alcohol of the formula (1) is referred to as "(R)-(1) referred to as "(S)-(1) alcohol", an R-form of an ester of the formula (2) is referred to as "(R)-(2) ester", and an S-form of an ester of the formula (2) is referred to as "(S)-(2) ester".

The optically active compounds (1) and (2) are intermediates of the optically active compound (3). That is, the optically active alcohol (1) is a compound wherein hydroxyl group on its aromatic ring is protected with the substituent $A^1$ to obtained the compound (2) wherein only hydroxyl group on its aromatic ring is protected is esterified. Also, only the substituent (protective group) $A^1$ is removed from the compound (2) by hydrolysis to easily form the optically active compound (3). Accordingly, it is necessary that the substituent $A^1$ can be easily removed from the compound (2) and the fission of the ester bond in the compound (2) is not caused upon removing the substituent $A^1$. For satisfying the above-mentioned requirements, in the present invention, the substituent $A^1$ is restricted to tetrahydro-2-pyranyl above-mentioned two groups is used as the substituent $A^1$, it is difficult to obtain the compound (3).

For removing the substituent $A^1$ from the compound (2), there are, for instance, used a mixed solvent of acetic acid, dioxane and water, and the like.

In the optically active compounds (1), (2) and (3), the group $R^1$ is an alkyl group having 1 to 15, preferably from 2 to 12, carbon atoms. The alkyl group $R^1$ may contain an asymmetric carbon atom. When the group $R^1$ is that having 16 or more carbon atoms, it cannot be expected that a liquid crystal composition obtained by adding an additive prepared from such a compound to liquid crystals has preferable performances as liquid crystals. Also, liquid crystal compositions obtained by adding the compound of the formula (4) in which $R^1$ is an alkyl group having more than 15 carbon atoms to liquid crystals have a high viscosity, therefore, the speed of response is slow. Also, compounds having groups other than the alkyl group instead of the group $R^1$ defined above cannot be expected to have excellent performances as liquid crystals. Also, they are apt to rapidly lower the thermal stability of the smectic phase when added to liquid crystals. The alkyl group used herein includes a halogenated alkyl group wherein hydrogen atom is substituted by a halogen atom, a group wherein an ether bond is introduced to the alkyl group, a group wherein an ester bond is introduced to the alkyl group. In addition to these groups, as the group $R^1$, there can be also used a residue of alkyl ethers having an asymmetric carbon, a residue of a lactic acid derivative, a residue of an amino acid derivative, a residue of a malic acid derivatives, and the like.

Concrete examples of the alkyl group $R^1$ are, for instance, methyl, ethyl, propyl, isopropyl, butyl, isobutyl, pentyl, 1- or 2-methylbutyl, hexyl, 1- or 3-methylpentyl, heptyl, 1- or 4-methylhexyl, octyl, 1-methylheptyl, nonyl, 1- or 6-methyloctyl, decyl, 1-methylnonyl, undecyl, 1-methyldecyl, dodecyl, 1-methylundecyl groups, and the like. The alkyl group $R^1$ is not limited to the exemplified groups. The alkyl group $R^1$ may contain an asymmetric carbon atom.

The optically active compound (3) is useful as a raw material of chiral dopants (additives) having a high compatibility with various known liquid crystals. Examples of the chiral dopants to be added to the smectic liquid crystals or the nematic liquid crystals are as follows:

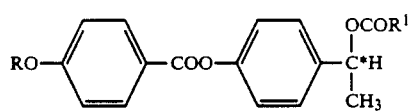

wherein R is an alkyl group having 1 to 15 carbon atoms and $R^1$ is as defined above,

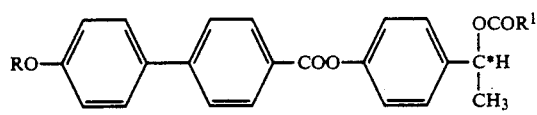

wherein R and $R^1$ are as defined above,

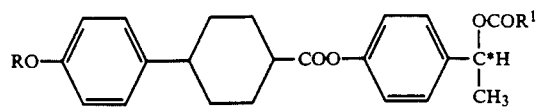

wherein R and $R^1$ are as defined above,

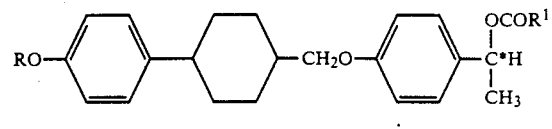

wherein R and $R^1$ are as defined above,

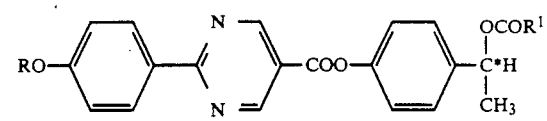

wherein R and $R^1$ are as defined above,

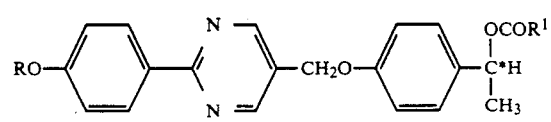

wherein R and $R^1$ are as defined above,

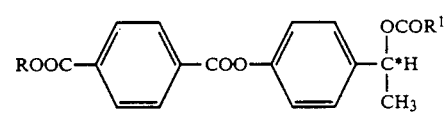

wherein R and $R^1$ are as defined above,

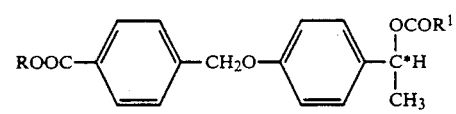

wherein R and $R^1$ are as defined above,

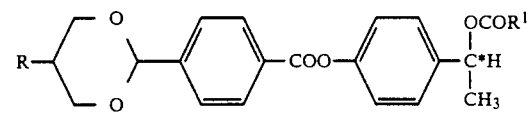

wherein R and $R^1$ are as defined above,

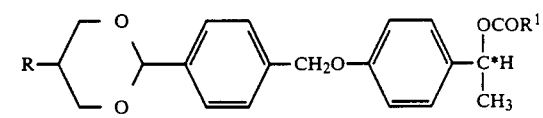

wherein R and $R^1$ are as defined above, and the like.

The chiral dopants can be prepared from the compound (3) as mentioned below. When the chiral dopants prepared from the compound (3) of the present invention is added to smectic liquid crystals or nematic liquid crystals, the obtained mixtures can realize a high Ps value in the smectic phase or the nematic phase, and a desired helical pitch.

Further, all of the optically active compounds (1), (2) and (3) are suitable for use of raw materials of medicines, agricultural chemicals, perfumery, and the like.

In the optically active compound of the present invention of the formula (4):

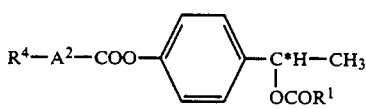 (4)

the group $R^4$ is an alkyl or alkyloxy group having 1 to 15 carbon atoms, preferably from 2 to 12 carbon atoms, the group $A^2$ is

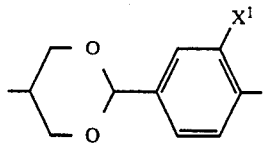

in which $X^1$ is hydrogen atom, a halogen atom or cyano group, or

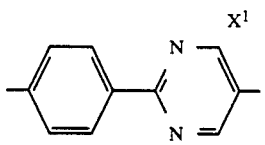

in which $X^1$ is as defined above.

When the group $R^4$ is those having 16 or more carbon atoms, liquid crystal compositions obtained by adding the compound (4) to liquid crystals have a high viscosity and, therefore, the response time is slow. Compounds having groups other than the alkyl and alkyloxy groups instead of the group $R^4$ defined above are not suitable, since they are apt to rapidly lower the thermal stability of the smectic phase when added to liquid crystals.

Examples of the alkyl group having 1 to 15 carbon atoms of the group $R^4$ are, for instance, methyl, ethyl, propyl, isopropyl, butyl, isobutyl, pentyl, 1- or 2-methylbutyl, hexyl, 1- or 3-methylpentyl, heptyl, 1- or 4-methylhexyl, octyl, 1-methylheptyl, nonyl, 1- or 6-methyloctyl, decyl, 1-methylnonyl, undecyl, 1-methyldecyl, dodecyl, 1-methylundecyl groups, and the like. The alkyl group $R^4$ is not limited to the exemplified groups. The alkyl group $R^4$ may contain an asymmetric carbon atom.

Examples of the alkyloxy group having 1 to 15 carbon atoms of the group $R^4$ are, for instance, methoxy, ethoxy, propoxy, isopropoxy, butoxy, isobutoxy, pentyloxy, 1- or 2-methylbutyloxy, hexyloxy, 1- or 3-methylpentyloxy, heptyloxy, 1- or 4-methylhexyloxy, octyloxy, 1-methylheptyloxy, nonyloxy, 1- or 6-methyloctyloxy, decyloxy, 1-methylnonyloxy, undecyloxy, 1-methyldecyloxy, dodecyloxy, 1-methylun- decyloxy groups, and the like. The alkyloxy group $R^4$ is not limited to the exemplified groups. The alkyloxy group $R^4$ may contain an asymmetric carbon atom.

In the formula (4), the group $A^2$ is

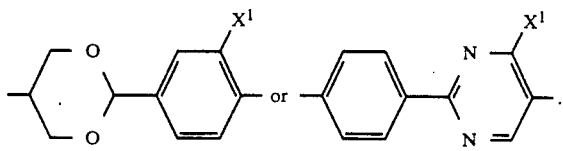

It can be considered that since the optically active compound (4) has such a group, the smectic phase required for forming ferroelectric liquid crystals can be easily shown.

Also, when $X^1$ is not any of hydrogen atom, halogen atoms and cyano group in the formula (4), it is difficult to obtain the ferroelectric liquid crystal composition by adding the compound having such a structure.

As to the optically active compound (4) having two asymmetric carbon atoms, there are (S,S)-form, (S,R)-form, (R,S)-form and (R,R)-form with respect to each asymmetric carbon atom.

It is preferable that the optical purity of the compound (4) is 100%, since the ferroelectric liquid crystal compositions can be obtained by adding a little amount (from 2 to 10% by weight) of the compound (4), and the influence concerning the phase transition temperature of smectic phase can be neglected. However, if the optical purity is not less than about 85%, the compounds (4) can be used without problems for obtaining the ferroelectric liquid crystal composition The optically active compounds (4) are usually white, though it varies depending on the number of carbon atoms of the group $R^4$, alkyl or alkyloxy.

The optically active compounds (4) have a high compatibility with many known liquid crystals, and therefore, they can be used in admixture therewith as a component of liquid crystal materials In particular, when the compounds (4) are added to smectic liquid crystals, the obtained mixtures can realize a high Ps value in the smectic phase.

The optically active compounds (1), (2), (3) and (4) can be prepared as follows:

The compound (3) is prepared by removing the protective group $A^1$ from the compound (2) obtained by asymmetrical transesterification of the racemic alcohol (5) with the fatty acid ester of 2,2,2-trichloroethanol or the vinyl ester (6) in the organic solvent in the presence of the enzyme having esterase activity.

The optically active compound (3) [optically active ester of fatty acid and 1-(p-hydroxyphenyl)ethanol] is prepared, for instance, by the following reaction formulas:

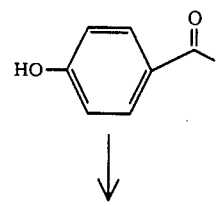

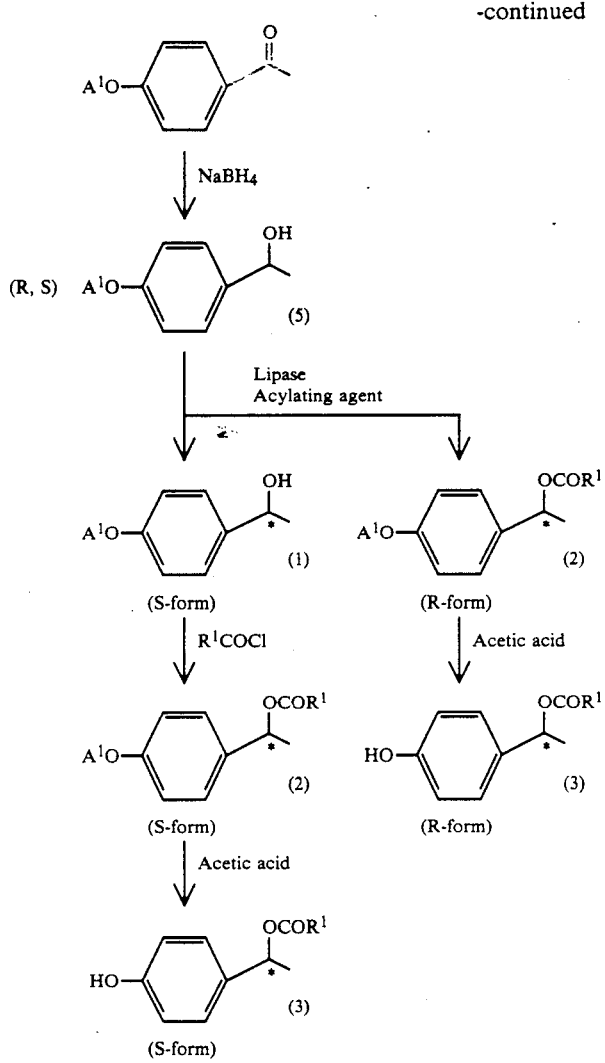

The optically active compounds (1) and (2) are prepared by subjecting a racemic alcohol having the formula (5):

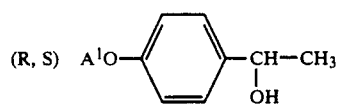

wherein $A^1$ is as defined above to optical resolution. The optically active alcohol of the formula (1) contains the S-form or the R-form of the alcohol. The optically active ester of the formula (2) is the fatty acid ester corresponding to the optically active alcohol (1). In the preparation process of the present invention, the racemic alcohol (5) is reacted with an ester of a fatty acid having 2 to 16 carbon atoms and 2,2,2-trichloroethanol or a vinyl ester of a fatty acid of the formula (6):

$$H_2C=CR^2-O-CO-R^3 \qquad (6)$$

wherein $R^2$ is hydrogen atom or methyl group and $R^3$ is an alkyl group having 1 to 8 carbon atoms in an organic solvent in the presence of an enzyme having esterase activity. Since the enzyme having esterase activity can selectively esterify only the R-form of the racemic alcohol (5), according to the above-mentioned reaction, the (R)-(2) ester and the (S)-(1) alcohol can be obtained. Also, the (R)-(2) ester can be converted into the (R)-(1) alcohol by hydrolysis using an alkali hydroxide such as KOH or NaOH, and on the other hand, the (S)-(1) alcohol can be converted into the (S)-(2) ester by esterification.

The preparation method of the racemic alcohol (5) are not particularly limited, and any methods can be conducted so long as the racemic alcohol (5) can be obtained.

For instance, the racemic alcohol of the formula (5) wherein $A^1$ is ethoxyethyl group can be obtained by protecting hydroxyl group of p-hydroxyacetophenone with ethyl vinyl ether, and reducing the obtained product with a reducing agent such as sodium boron hydride. Similarly, the racemic alcohol of the formula (5) wherein $A^1$ is tetrahydro-2-pyranyl group can be obtained by protecting hydroxyl group of p-hydroxyacetophenone with dihydropirane:

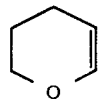

and reducing.

The ester of the fatty acid having 2 to 16 carbon atoms and 2,2,2-trichloroethanol or the vinyl ester of fatty acid of the formula (6):

$$H_2C=CR^2-O-CO-R^3 \qquad (6)$$

wherein $R^2$ is hydrogen atom or methyl group and $R^3$ is an alkyl group having 1 to 8 carbon atoms are used as the acylating agent in the above reaction. The number of carbon atoms of the fatty acid in the fatty acid ester of 2,2,2-trichloroethanol or the vinyl ester (6) corresponds to the number of carbon atoms of the group $R^1$ in the compounds (2) and (3), so the desired product can be obtained by suitably selecting and using the fatty acid having the desired number of carbon atoms.

Examples of the fatty acid ester of 2,2,2-trichloroethanol are, for instance, 2,2,2-trichloroethyl acetate, 2,2,2-trichloroethyl butyrate, 2,2,2-trichloroethyl heptanoate, and the like.

Examples of the vinyl ester of fatty acid are, for instance, isopropenyl acetate, vinyl acetate, vinyl valerate, vinyl octanoate, and the like.

As to the vinyl ester of fatty acid (6), when the number of carbon atoms of the alkyl group $R^3$ is 9 or more, it is difficult to synthesize esters of the formula (6) wherein $R^3$ is an alkyl group having 9 or more carbon atoms, and such a synthesis is economically disadvantageous.

As the enzyme having esterase activity, any enzyme can be used without any restriction so long as the enzyme can asymmetrically esterify only the R-form of the racemic alcohol (5). Both enzymes derived from microorganisms and enzymes derived from animals can be used. Also enzymes which are put on the market or not can be used.

Examples of the enzymes derived from the microorganisms are, for instance, enzymes produced from microorganisms belonging to Pseudomonas (*Pseudomonas aeruginosa*), Achromobacterium (*Achromobacterium viscosm*) or Candida (*Candida cylindracea*). Examples of the enzymes derived from the animals are, for instance, enzymes produced from a pancreas of pigs. The enzymes used in the present invention are not limited thereto.

Examples of the enzymes put on the market are, for instance, "Lipase Amano P" (trade mark) commercially available from Amano Seiyaku Kabushiki Kaisha, "Lipase Toyo" (trade mark) commercially available from Toyo Jozo Kabushiki Kaisha, "Pancreatin Lipase" (trade mark) commercially available from Amano Seiyaku Kabushiki Kaisha, "Pancreatin Lipase" (trade mark) commercially available from SIGUMA Chemical Company, "Lipase B" (trade mark) commercially available from Wako Junyaku Kabushiki Kaisha, "Lipase MY" (trade mark) commercially available from Meito Sangyo Kabushiki Kaisha, and the like.

Any organic solvent can be used in the optical resolution without particular restriction so long as the racemic alcohol (5) and the acylating agent can be dissolved therein and the esterase activity of the enzyme is not prevented. Examples of the organic solvent are, for instance, diethyl ether, methyl ethyl ether, diisopropyl ether, n-hexane, cyclohexane, n-heptane, toluene, and the like.

The solution containing the racemic alcohol (5), the acylating agent and the enzyme having esterase activity in the organic solvent can be prepared in any method without particular restriction. For instance, it is possible that the racemic alcohol (5), the acylating agent and the enzyme having esterase activity are added at once to the organic solvent to give the solution. Also, it is possible that the solution or dispersion of the racemic alcohol (5), the solution or dispersion of the acylating agent and the solution or dispersion of the enzyme are prepared, respectively, and they are mixed to give the desired solution. Further, it is possible that the solution of one which is hardly dissolved in the solvent but can be dissolved by heating is first obtained and another solution is added thereto.

It is preferable that the amount of the acylating agent to the racemic alcohol (5) is from 0.5 to 2.0 moles, more preferably from 1 to 1.5 moles, per mole of the alcohol (5). When the amount of the acylating agent is less than 0.5 mole per mole of the alcohol (5), all of the R-form of the racemic alcohol (5) cannot be converted into the ester since the molar amount of the acylating agent is smaller that that of the R-form of the alcohol (5). On the other hand, when the amount of the acylating agent is more than 2 moles per mole of the alcohol (5), the amount of the acylating agent which does not participate in the reaction increases, so it is economically disadvantageous.

It is preferable that the amount of the enzyme having esterase activity is from 10 to 600 g, preferably from 100 to 500g, per mole of the racemic alcohol (5). When the amount of the enzyme is less than 10 g, the reaction rate is so slow that it is economically disadvantageous. On the other hand, when the amount of the enzyme is more than 600 g, the reaction rate cannot be made high for the amount of the used enzyme, so it is economically disadvantageous.

It is preferable that the concentration of the sum of racemic alcohol (5) and the acylating agent is from 0.1 to 50% by weight, preferable from 10 to 30% by weight, based on the weight of the solution. When the concentration is less than 0.1% by weight, the yield of the obtained product is low for the amount of the used solution, so it is economically disadvantageous. On the other hand, when the concentration is more than 50% by weight, the reaction rate is lowered depending on the too high concentration to lower the yield.

The reaction is conducted at a temperature of, usually 10° to 40° C., preferably 25° to 30° C., since the enzyme having esterase activity is used.

The reaction time varies depending on the kinds of the racemic alcohol (5) and the enzyme having esterase activity, the ratio of the used alcohol (5) to the used enzyme and reaction conditions such as stirring condition, so it cannot be generally decided. Usually, it is preferable that the reaction time is from 1 to 150 hours, preferably from 24 to 96 hours.

The finish of the reaction can be confirmed by measuring a conversion of the racemic alcohol (5) to the ester according to gas chromatography, that is, the reaction is finished when the conversion is constant.

The thus obtained reaction mixture is filtered to remove the enzyme having esterase activity. Then, after removing the organic solvent as occasion demands, the (R)-(2) ester is separated from the (S)-(1) alcohol, for instance, by using silica gel column chromatography. Further, if the obtain product contains alcohols produced by acylation or the unreacted acylating agent, the purification such as evaporation is conducted. As the developing solvent used in the column chromatography, there can be used a mixture of ethyl acetate and n-hexane (ethyl acetate/n-hexane: ¼ to 1/20 by volume), a mixture of chloroform and methanol (chloroform/methanol: 1/10 to 1/40 by volume), and the like.

The used enzyme separated from the reaction mixture can be used again.

The identification of the compounds (1) and (2) can be conducted by the measurements of $^1$H-NMR spectrum, IR spectrum and specific rotation.

Then the obtained (R)-(2) ester is chemically or enzymatically hydrolyzed to give easily the (R)-(1) alcohol which is an enantiomer of the (S)-(1) alcohol. Also, the (S)-(1) alcohol is esterified to give the (S)-(2) ester which is an enantiomer of the (R)-(2) ester.

Thus, the optically active compounds (1) and (2) can be obtained in yields of 80 to 90%.

The optically active compound (2) can be easily converted into the optically active compound (3) (the fatty acid ester of p-hydroxyphenylethanol) by removing the protective group A$^1$.

Then, the optically active compound of the formula (4):

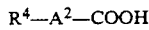

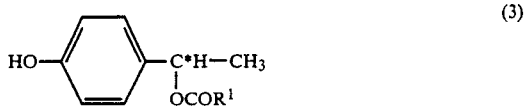

wherein R$^4$ and A$^2$ are as defined above, to esterification with the compound of the formula (3):

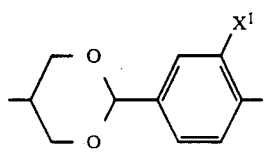

wherein R$^1$ is as defined above.

For instance, the compound of the formula (4) in which R$^4$ is an alkyl group and A$^2$ is

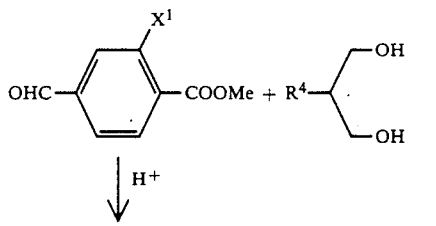

is prepared, for instance, by the following reaction formulas:

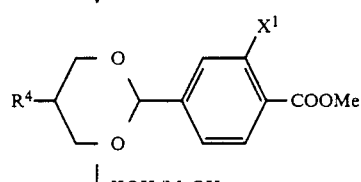

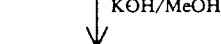

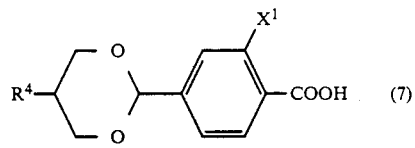

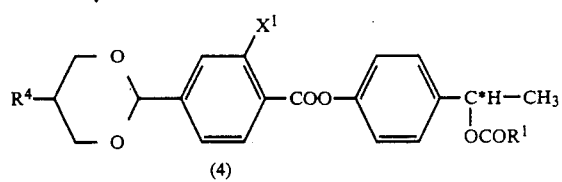

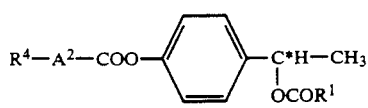

wherein A$^2$, R$^1$ and R$^4$ are as defined above, is prepared by subjecting a compound of the formula (7):

That is, methyl ester of terephthalaldehydric acid is reacted with a diol having an alkyl group which corresponds to the group R$^4$ of the desired compound (4) to give a trans-2-(p-carbomethoxyphenyl)-5-alkyl-1,3-dioxane. Then, the dioxane is hydrolyzed with KOH/MeOH (1 equivalent) to give a compound of the formula (7). Finally, the compound (7) is reacted with the fatty acid ester of 1-(p-hydroxyphenyl)ethanol of the formula (3) to give a desired compound (4).

Also, the compound of the formula (4) wherein $A^2$ is

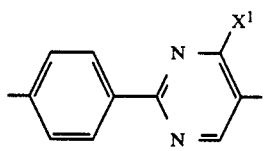

is prepared, for instance, by the following reaction formulas:

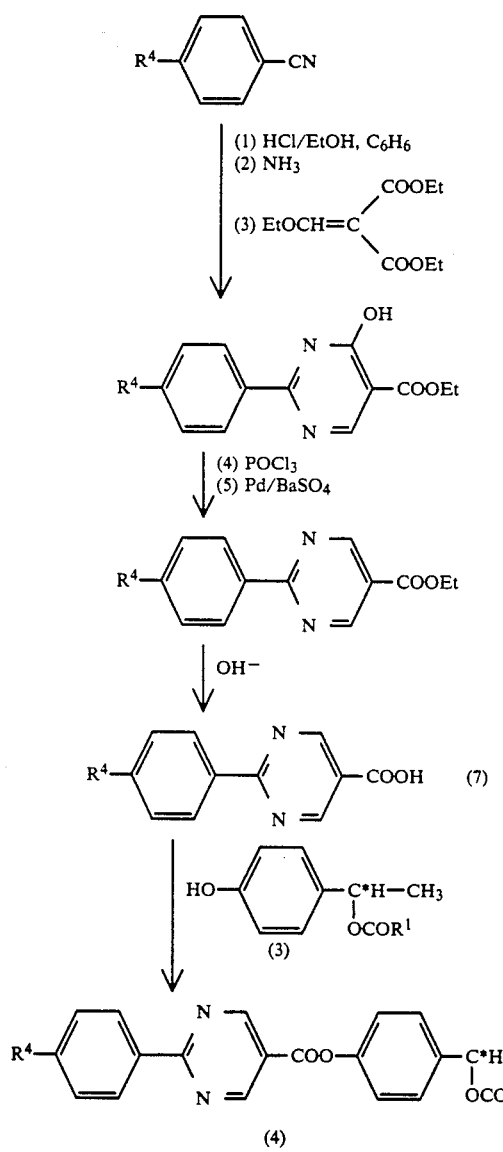

That is, hydrogen chloride gas passes through a p-alkyloxy or p-alkyl cyanobenzene in a mixture of absolute ethanol and anhydrous benzene to give an imide ethyl ether [reaction (1)], then the ether is reacted with ammonia gas in ethanol to give a p-alkyloxy or p-alkyl phenylamidine hydrochloride [reaction (2)], and the hydrochloride is reacted with diethyl ethoxymethylene malonate in a sodium ethylate solution (sodium/EtOH) to give an ethyl 2-(p-alkyloxyphenyl)-4-hydroxypyrimidinecarboxylate or ethyl 2-(p-alkylphenyl)-4-hydroxypyrimidine-5-carboxylate [reaction (3)]. After the hydroxyl group at the 4-position of the pyrimidine ring is halogenated (chloronated) with POCl₃ [reaction (4)], hydrogenation is conducted with Pd/BaSO₄ to give an ethyl 2-(p-alkyloxyphenyl)pyrimidine-5-carboxylate or ethyl 2-(p-alkylphenyl)pyrimidine-5-carboxylate [reaction (5)]. The obtained carboxylate is hydrolyzed in KOH/MeOH (1N solution) to give a 2-(p-alkyloxyphenyl)-pyrimidine-5-carboxylic acid or a 2-(p-alkylphenyl)-pyrimidine-5-carboxylic acid of the formula (7). The esterification of the compound (7) with the fatty acid ester of 1-(p-hydroxyphenyl)ethanol of the formula (3) is conducted to give a desired compound (4).

The esterification of the compound (7) and the compound (3) can be conducted in any known method such as DCC method or acid chloride method, and the optically active compound (4) can be prepared in a yield of 80 to 90%.

The present invention is more specifically described and explained by means of the following Examples in which all % and parts are by weight unless otherwise noted. It is to be understood that the present invention is not limited to the Examples.

In each Example, a compound having two asymmetric carbon atoms is expressed, for convenience sake, as a (S,S)-form, (S,R)-form, (R,S)-form or (R,R)-form which is an absolute configuration which can be naturally expected from its starting materials, so an absolute configuration of the compound is not decided.

Also, in an optical resolution using an enzyme, an enantiomer obtained by conducting transesterification with a fatty acid ester of 2,2,2-trichloroethanol or a vinyl ester (6) is expressed as an R-form according to the descriptions of Journal of American Chemical Society, 107, 7072 (1985).

EXAMPLE 1

[Preparation of 1-(4-(1-ethoxyethoxy)phenyl)ethanol]

(i) First, 4-(1-ethoxyethoxy)acetophenone was prepared as mentioned below.

In 100 ml of diethyl ether was dissolved 13.6 g (0.1 mole) of p-hydroxyacetophenone and ethyl vinyl ether, 1 ml of concentrated hydrochloric acid was added to the obtained solution, and the mixture was refluxed for 4 hours and then was subjected to reaction at room temperature for 16 hours. The reaction mixture was washed with 50 ml of 0.1 N aqueous solution of sodium hydroxide 2 times and then with water 3 times. The resulting ether layer was dried with anhydrous magnesium sulfate and ether was distilled under reduced pressure to give 20.5 g of 4-(1-ethoxyethoxy)acetophenone (yield: 92

The δ values (ppm) of ¹H-NMR spectrum of the product (300 MHz, CDCl₃) were as follows:

1.17 (t, 3H), 1.51 (d, 3H),
2.52 (s, 3H), 3.50 (m, 1H),
3.72 (m, 1H), 5.48 (q, 1H),
6.95 (d, 2H), 7.88 (d, 2H)

(ii) Then, 1-(4-(1-ethoxyethoxy)phenyl)ethanol was prepared as mentioned below. 7 In 100 ml of ethanol was dissolved 15.0 g (72 millimoles) of 4-(1-ethoxyethoxy)acetophenone as obtained in Example (i), to which 2.2 g (58 millimoles) of NaBH₄ was added, and the mixture was subjected to reaction for 5 hours. After ethanol was distilled under reduced pressure, 200 ml of ether was added thereto, and the resulting mixture was washed with diluted hydrochloric acid, then water and finally an aqueous solution of sodium hydrogencarbonate. The resulting ether layer was dried with anhydrous magnesium sulfate and the solvent was distilled under reduced pressure to give 13.6 g of 1-(4-(1-ethoxyethoxy)phenyl)ethanol (yield: 90%).

The δ values (ppm) of $^1$H-NMR spectrum of the product (300 MHz, CDCl$_3$) were as follows:
1.17 (t, 3H), 1.44 (d, 3H),
1.46 (d, 3H), 1.93 (s, 1H),
3.52 (m, 1H), 3.76 (m, 1H),
4.82 (m, 1H), 5.34 (q, 1H),
6.94 (d, 2H), 7.27 (d, 2H)

EXAMPLE 2

[Optical resolution of 1-(4-(1-ethoxyethoxy)phenyl)ethanol]

(i) First, transesterification with 2,2,2-trichloroethyl butyrate was conducted as mentioned below.

To 120 ml of anhydrous diethyl ether was added 21 g (0.1 mole) of 1-(4-(1-ethoxyethoxy)phenyl)ethanol, 22.4 g (0.1 mole) of 2,2,2-trichloroethyl butyrate and 25.2 g of Lipase P (commercially available from Amano Seiyaku Kabushiki Kaisha) and the mixture was reacted with stirring at 25° C. for 90 hours. The reaction mixture was filtered by suction to remove Lipase P, the filtrate was concentrated and the concentrate was then purified by silica gel chromatography [ethyl acetate/n-hexane = ¼ by volume (hereinafter the same)] to give 9.6 g of S-form of 1-(4-(1-ethoxyethoxy)phenyl)ethanol (yield: 91%) and 13.0 g of R-form of 1-(4-(1-ethoxyethoxy)phenyl)ethyl butyrate (yield: 93%).

As to the obtained each product, the results of $^1$H-NMR spectrum analysis, IR spectrum analysis and the specific rotation, $[\alpha]_D^{20}$ are shown as follows:

S-form of 1-(4-(1-ethoxyethoxy)phenyl)ethanol $^1$H-NMR [300 MHz, CDCl$_3$, δ value (ppm)]1.17 (t, 3H), 1.44 (d, 3H), 1.46 (d, 3H), 1.93 (s, 1H), 3.52 (m, 1H), 3.76 (m, 1H), 4.82 (m, 1H), 5.34 (q, 1H), 6.94 (d, 2H), 7.27 (d, 2H)

FT-IR (cm$^{-1}$) 3398, 2974, 2931, 2889, 1612, 1512, 1446, 1381, 1342, 1238, 1176, 1134, 1118, 1076, 1049, 1010, 945, 898, 837

$[\alpha]_D^* = -36.1°$ (CHCl$_3$, c=1)

R-form of 1-(4-(1-ethoxyethoxy)phenyl)ethyl butyrate $^1$H-NMR [300MHz, CDCl$_3$, δ value (ppm)]0.90 (t, 3H), 1.19 (t, 3H), 1.47 (d, 3H), 1.49 (d, 3H), 1.62 (m, 2H), 2.27 (t, 2H), 3.51 (m, 1H), 3.76 (m, 1H), 5.35 (q, 1H), 5.84 (q, 1H), 6.94 (d, 2H), 7.26 (d, 2H)

FT-IR (cm$^{-1}$) 2974, 2935, 2877, 1735, 1612, 1585, 1512, 1454, 1419, 1381, 1346, 1288, 1176, 1134, 1099, 1076, 1060, 1014, 1003, 941, 898, 833, 551

$[\alpha]_D^{20} = +84.0°$ (CHCl$_3$, c=1)

(ii) The procedure of Example 2 (i) was repeated except that 2,2,2-trichloroethyl heptanoate was used instead of 2,2,2-trichloroethyl butyrate to give 9.5 g of S-form of 1-(4-(1-ethoxyethoxy)phenyl)ethanol (yield: 90%) and 14.8 g of R-form of 1-(4-(1-ethoxyethoxy)phenyl)ethyl heptanoate (yield: 92%).

As to the obtained each compound, the results of $^1$H-NMR spectrum analysis, FT-IR spectrum analysis and the specific rotation, $[\alpha]_D^{20}$ are shown as follows:
As to the S-form of 1-(4-(1-ethoxyethoxy)phenyl)ethanol, the same results as those of the S-form obtained in Example 2 (i) were obtained in $^1$H-NMR spectrum analysis and IR spectrum analysis.

$[\alpha]_D^{20} = -36.1°$ (CHCl$_3$, c=1)

R-form of 1-(4-(1-ethoxyethoxy)phenyl)ethyl heptanoate $^1$H-NMR [300MHz, CDCl$_3$, δ value (ppm)]0.84 (t, 3H), 1.19 (t, 3H), 1.24 (m, 6H), 1.47 (d, 3H), 1.49 (d, 3H), 1.58 (m, 2H), 2.28 (t, 2H), 3.49 (m, 1H), 3.76 (m, 1H), 5.35 (q, 1H), 5.83 (q, 1H), 6.94 (d, 2H), 7.25 (d, 2H)

FT-IR (cm$^{-1}$) 2978, 2958, 2931, 2870, 2858, 1735, 1612, 1585, 1512, 1454, 1419, 1377, 1342, 1288, 1238, 1168, 1134, 1118, 1099, 1076, 1057, 1014, 1003, 941, 898, 833, 551

$[\alpha]_D^{20} = +69.0°$ (CHCl$_3$, c=1)

(iii) The procedure of Example 2 (i) was repeated except that vinyl valerate was used instead of 2,2,2-trichloroethyl butyrate to give 9.8 g of S-form of 1-(4-(1-ethoxyethoxy)phenyl)ethanol (yield: 93%) and 11.8 g of R-form of 1-(4-(1-ethoxyethoxy)phenyl)ethyl valerate (yield: 94%).

As to the obtained each compound, the results of $^1$H-NMR spectrum analysis, IR-spectrum analysis and the specific rotation, $[\alpha]_D^{20}$ are shown as follows:

As to the S-form of 1-(4-(1-ethoxyethoxy)enyl)ethanol, the same results as those of the S-form obtained in Example 2 (i) were obtained in $^1$H-NMR spectrum analysis and FT-IR spectrum analysis.

$[\alpha]_D^{20} = -36.1°$ (CHCl$_3$, c=1)

R-form of 1-(4-(1-ethoxyethoxy)phenyl)ethyl valerate $^1$H-NMR [300MHz, CDCl$_3$, δ value (ppm)]0.86 (t, 3H), 1.19 (t, 3H), 1.26 (m, 2H), 1.47 (d, 3H), 1.49 (d, 3H), 1.59 (m, 2H), 2.28 (t, 2H), 3.50 (m, 1H), 3.76 (m, 1H), 5.35 (q, 1H), 5.83 (q, 1H), 6.94 (d, 2H), 7.25 (d, 2H)

FT-IR (cm$^{-1}$) 2974, 2935, 2877, 1735, 1612, 1585, 1512, 1454, 1419, 1381, 1346, 1288, 1238, 1176, 1134, 1099, 1076, 1060, 1014, 1003, 941, 898, 833, 551

$[\alpha]_D^{20} = +80.2°$ (CHCl$_3$, c=1)

(iv) R-form of 1-(4-(1-ethoxyethoxy)phenyl)ethanol was prepared as mentioned below.

In 210 ml of 1N ethanol solution of potassium hydroxide was dissolved 28 g (0.1 mole) of the R-form of 1-(4-(1-ethoxyethoxy)phenyl)ethyl butyrate obtained in Example 2 (i), (ii) or (iii), the mixture was reacted at room temperature over night, and the reaction mixture was concentrated under reduced pressure To the residue was added 200 ml of ether, and it was washed with 2N aqueous solution of sodium hydroxide 2 times and then with water 3 times. The resulting ether layer was dried with anhydrous magnesium sulfate and ether was distilled under reduced pressure. The residue was purified by silica gel chromatography (ethyl acetate/n-hexane=¼) to give 18.9 g of R-form of 1-(4-(1-ethoxythyoxy)phenyl)ethanol (yield: 90%).

As to the obtained compound, the results of $^1$H-NMR spectrum analysis, IR spectrum analysis and the specific rotation, $[\alpha]_D^{20}$ are as follows:

The same results as those of the compound obtained in Example 2 (i) were obtained in $^1$H-NMR spectrum analysis and FT-IR spectrum analysis.

$[\alpha]_D^{20} = +36.9°$ (CHCl$_3$, c=1)

EXAMPLE 3

(i) An S-form of a fatty acid ester of 1-(4-(1-ethoxyethoxy)phenyl)ethanol was prepared as mentioned below.

In 50 ml of pyridine was dissolved 0.05 mole of the S-form of 1-(4-(1-ethoxyethoxy)phenyl)ethanol, and 0.06 mole of an acid chloride of a fatty acid [butanoic (butyric) acid, hexanoic acid, heptanoic acid or decanoic acid] was gradually added dropwise to the mixture. After finishing the addition, the reaction was further continued for 10 hours, and the reaction mixture was concentrated under reduced pressure. To the residue was added 100 ml of diethyl ether, and it was washed with diluted hydrochloric acid, then water and finally 10% aqueous solution of sodium hydrogencarbonate. The resulting ether layer was dried with anhydrous magnesium sulfate and ether was distilled under reduced pressure to give an S-form of the fatty acid ester (which corresponded to the used acid chloride) of 1-(4-(1-ethoxyethoxy)phenyl)ethanol.

The results of the yield and the specific rotation, $[\alpha]_D^{20}$ of the obtained each compound are shown in Table 1.

Also, the results of $^1$H-NMR spectrum analysis and IR spectrum analysis are shown as follows:

S-form of 1-(4-(1-ethoxyethoxy)phenyl)ethyl butyrate $^1$H-NMR [300MHz, CDCl$_3$, δ value (ppm)]0.90 (t, 3H), 1.19 (t, 3H), 1.47 (d, 3H), 1.49 (d, 3H), 1.62 (m, 2H), 2.27 (t, 2H), 3.51 (m, 1H), 3.76 (m, 1H), 5.35 (q, 1H), 5.84 (q, 1H), 6.94 (d, 2H), 7.26 (d, 2H)

FT-IR (cm$^{-1}$) 2974, 2935, 2877, 1735, 1612, 1585, 1512, 1454, 1419, 1381, 1346, 1288, 1238, 1176, 1134, 1099, 1076, 1060, 1014, 1003, 941, 898, 833, 551

S-form of 1-(4-(1-ethoxyethoxy)phenyl)ethyl hexanoate $^1$H-NMR [300MHz, CDCl$_3$, δ value (ppm)]0.85 (t, 3H), 1.19 (t, 3H), 1.27 (m, 4H), 1.47 (d, 3H), 1.49 (d, 3H), 1.59 (m, 2H), 2.28 (t, 2H), 3.50 (m, 1H), 3.76 (m, 1H), 5.35 (q, 1H), 5.83 (q, 1H), 6.94 (d, 2H), 7.25 (d, 2H)

FT-IR (cm$^{-1}$) 2978, 2958, 2931, 2870, 1735, 1612, 1585, 1512, 1454, 1377, 1342, 1288, 1242, 1172, 1122, 1057, 1014, 945, 898, 833, 551

S-form of 1-(4-(1-ethoxyethoxy)phenyl)ethyl heptanoate $^1$H-NMR [300MHz, CDCl$_3$, δ value (ppm)]0.84 (t, 3H), 1.19 (t, 3H), 1.24 (m, 6H), 1.47 (d, 3H), 1.49 (d, 3H), 1.58 (m, 2H), 2.28 (t, 2H), 3.49 (m, 1H), 3.76 (m, 1H), 5.35 (q, 2H), 5.83 (q, 1H), 6.94 (d, 2H), 7.25 (d, 2H)

FT-IR (cm$^{-1}$) 2978, 2958, 2931, 2870, 2858, 1735, 1612, 1585, 1512, 1454, 1419, 1377, 1342, 1288, 1238, 1168, 1134, 1118, 1099, 1076, 1057, 1014, 1003, 941, 898, 833, 551

S-form of 1-(4-(1-ethoxyethoxy)phenyl)ethyl decanoate $^1$H-NMR [300MHz, CDCl$_3$, δ value (ppm)]0.85 (t, 1H), 1.19 (t, 3H), 1.23 (m, 12H), 1.47 (d, 3H), 1.49 (d, 3H), 1.58 (m, 1H), 2.28 (t, 2H), 3.54 (m, 1H), 3.75 (m, 1H), 5.35 (q, 1H), 5.83 (q, 1H), 6.94 (d, 2H), 7.25 (d, 2H)

FT-IR (cm$^{-1}$) 2978, 2954, 2927, 2854, 1735, 1612, 1585, 1512, 1458, 1419, 1377, 1300, 1288, 1238, 1176, 1118, 1076, 1057, 1014, 1003, 941, 902, 833, 551

(ii) An S-form of a fatty acid ester of 1-(4-hydroxyphenyl)ethanol was prepared as mentioned below.

In about 200 ml of a mixed solvent of acetic acid/dioxane/water (10/5/5 by volume) was dissolved 0.1 mole of each of the S-form of fatty acid ester of 1-(4-(1-ethoxyethoxy)phenyl)ethanol obtained in Example 3 (i), and the mixture was stirred at room temperature for 2 hours. The solvent was distilled under reduced pressure to give an S-form of fatty acid ester of 1-4-hydroxyphenyl)ethanol.

The yield and the specific rotation of the obtained each ester are shown in Table 1.

The results of $^1$H-NMR analysis, and IR spectrum analysis are shown as follows:

S-form of 1-(4-hydroxyphenyl)ethyl butyrate $^1$H-NMR [300MHz, CDCl$_3$, δ value (ppm)]0.89 (t, 3H), 1.50 (d, 3H), 1.61 (m, 2H), 2.28 (t, 2H), 5.83 (q, 1H), 6.14 (broad s, 1H), 6.77 (d, 2H), 7.20 (d, 2H)

FT-IR (cm$^{-1}$) 3387, 2970, 2935, 2873, 1732, 1705, 1616, 1597, 1516, 1450, 1373, 1265, 1199, 1172, 1091, 1057, 999, 956, 941, 833, 547

S-form of 1-(4-hydroxyphenyl)ethyl hexanoate $^1$H-NMR [300MHz, CDCl$_3$, δ value (ppm)]0.85 (t, 3H), 1.25 (m, 4H), 1.49 (d, 3H), 1.59 (m, 2H), 2.28 (t, 2H), 5.74 (broad s, 1H), 5.67 (q, 1H), 6.77 (d, 2H), 7.20 (d, 2H)

FT-IR (cm$^{-1}$) 3371, 3024, 2958, 2931, 2870, 1732, 1705, 1616, 1597, 1516, 1450, 1415, 1357, 1288, 1265, 1242, 1222, 1211, 1168, 1099, 1057, 1014, 1003, 956, 833, 729, 547

S-form of 1-(4-hydroxyphenyl)ethyl heptanoate $^1$H-NMR [300MHz, CDCl$_3$, δ value (ppm)]0.85 (t, 3H), 1.23 (m, 6H), 1.48 (d, 3H), 1.57 (m, 2H), 2.28 (t, 2H), 5.83 (q, 1H), 5.91 (broad s, 1H), 6.77 (d, 2H), 7.22 (d, 2H)

FT-IR (cm$^{-1}$) 3390, 3024, 2954, 2931, 2858, 1732, 1706, 1616, 1597, 1516, 1450, 1377, 1269, 1222, 1168, 1099, 1057, 999, 949, 833, 725, 644, 547

S-form of 1-(4-hydroxyphenyl)ethyl decanoate $^1$H-NMR [300MHz, CDCl$_3$, δ value (ppm)]0.85 (t, 3H), 1.23 (m, 12H), 1.49 (d, 2H), 1.58 (m, 2H), 2.28 (t, 2H), 5.51 (broad s, 1H), 5.82 (q, 1H), 6.77 (d, 2H), 7.20 (d, 2H)

FT-IR (cm,-1) 3394, 3024, 2927, 2854, 1732, 1705, 1616, 1597, 1516, 1450, 1377, 1269, 1207, 1168, 1111, 1057, 999, 952, 833, 721, 547

(iii) An R-form of fatty acid ester of 1-(4-(1-ethoxyethoxy)phenyl ethanol was prepared as mentioned below.

The procedure of Example 3 (i) was repeated except that the R-form of 1-(4-(1-ethoxyethoxy)phenyl)ethanol was used to give an R-form of fatty acid ester of 1-(4-(1-ethoxyethoxy)phenyl)ethanol (which corresponds to the used acid chloride).

As to the obtained each compound, the same results as those of the compound obtained in Example 3 (i) were obtained in $^1$H-NMR spectrum analysis and FT-IR spectrum analysis.

(iv) An R-form of fatty acid ester of 1-(4-hydroxyphenyl)ethanol was prepared as mentioned below.

In 700 ml of a mixed solvent of acetic acid/dioxane/water (10/5/5) was dissolved 0.35 mole of a each R-form of fatty acid ester of 1-(4-(1-ethoxyethoxy)phenyl)ethanol, and the mixture was stirred at room temperature for 2 hours. The solvent was distilled under reduced pressure to give an R-form of fatty acid ester of 1-(4-hydroxyphenyl)ethanol.

As to the obtained butyrate and heptanoate, the same results as those of the S-form of the fatty acid ester of 1-(4-hydroxyphenyl)ethanol in Example 3 (ii) were obtained in $^1$H-NMR spectrum analysis and FT-IR spectrum analysis.

Also, as to the valerate, the results of $^1$H-NMR spectrum analysis are shown as follows:

$^1$H-NMR [300MHz, CDCl$_3$, δ value (ppm)]0.85 (t, 3H), 1.26 (m, 2H), 1.47 (d, 3H), 1.59 (m, 2H), 2.28 (t, 2H), 5.71 (broad s, 1H), 5.82 (q, 1H), 6.94 (d, 2H), 7.25 (d, 2H)

As to the obtained compound, the results of $^1$H-NMR spectrum analysis are shown as follows:

$^1$H-NMR [300MHz, CDC±3, δ value (ppm)]1.46 (d, 3H), 1.63 (m, 3H), 1.84 (m, 2H), 1.97 (m, 1H), 3.68 (m, 1H), 3.89 (m, 1H), 4.83 (q, 1H), 5.39 (t, 1H), 7.02 (d, 2H), 7.27 (d, 2H)

EXAMPLE 5

[Optical resolution of 1-(4-(tetrahydro-2-pyranyloxy)phenyl)ethanol]

(i) The asymmetrical transesterification with 2,2,2-tri-

TABLE 1

| | Compound | Yield (%) | Specific rotation ($[α]_D^{20}$ CHCl$_3$, c = 1) |
|---|---|---|---|
| Ex. 3 (i) | 1-(4-(1-ethoxyethoxy)phenyl)ethyl butyrate (S-form) | 91 | −83.5° |
| | 1-(4-(1-ethoxyethoxy)phenyl)ethyl hexanoate (S-form) | 92 | −74.0° |
| | 1-(4-(1-ethoxyethoxy)phenyl)ethyl heptanoate (S-form) | 90 | −68.1° |
| | 1-(4-(1-ethoxyethoxy)phenyl)ethyl decanoate (S-form) | 93 | −59.0° |
| Ex. 3 (ii) | 1-(4-hydroxyphenyl)ethyl butyrate (S-form) | 85 | −109.8° |
| | 1-(4-hydroxyphenyl)ethyl hexanoate (S-form) | 89 | −85.0° |
| | 1-(4-hydroxyphenyl)ethyl heptanoate (S-form) | 92 | −79.3 |
| | 1-(4-hydroxyphenyl)ethyl decanoate (S-form) | 88 | −77.0° |
| Ex. 3 (iv) | 1-(4-hydroxyphenyl)ethyl butyrate (R-form) | 90 | +110.1° |
| | 1-(4-hydroxyphenyl)ethyl heptanoate (R-form) | 90 | +80.1° |
| | 1-(4-hydroxyphenyl)ethyl valerate (R-form) | 89 | +97.1° |
| | 1-(4-hydroxyphenyl)ethyl decanoate (R-form) | 87 | +72.2° |
| | 1-(4-hydroxyphenyl)ethyl hexanoate (R-form) | 91 | +85.9° |

EXAMPLE 4

[Preparation of 1-(4-(tetrahydro-2-pyranyloxy)phenyl)ethanol]

(i) First, 4-(tetrahydro-2-pyranyloxy)acetophenone was prepared as mentioned below.

In 150 ml of dichloromethane was dissolved 13.6 g (0.1 mole) of p-hydroxyacetophenone and 12.5 g of 3,4-dihydro-α-pyrane, to which 1.1 g of pyrimidium ptoluenesulfonate was added, and the mixture was subjected to reaction at room temperature over night. The reaction mixture was washed with 50 ml of 0.5 N aqueous solution of sodium hydroxide 3 time and then with water 3 times. The resulting ether layer was dried with anhyrous magnesium sulfate, and ether was distilled under reduced pressure to give 20.5 g of oily 4-(tetrahydro-2-pyranyloxy)acetophenone (yield: 93%).

As to the obtained compound, the results of $^1$H-NMR spectrum analysis are shown as follows:

$^1$H-NMR [300MHz, CDCl$_3$, δ value (ppm)]1.68 (m, 3H), 1.86 (m, 2H), 1.98 (m, 1H), 2.53 (s, 3H), 3.60 (m, 1H), 3.82 (m, 1H), 5.50 (t, 1H), 7.07 (d, 2H), 7.91 (d, 2H)

(ii) 1-(4-(tetrahydro-2-pyranyloxy)phenyl)ethanol was prepared as mentioned below.

In 200 ml of ethanol was dissolved 22.0 g (0.1 mole) of 4-(tetrahydro-2-pyranyloxy)acetophenone obtained in Example 4 (i), to which 2.3 g (58 millimoles) of NaBH$_4$ was added, and the mixture was subjected to reaction for 3 hours at 25° C. After ethanol was distilled under reduced pressure, 200 ml of ethanol was added thereto, and it was washed with diluted hydrochloric acid, then water and finally an aqueous solution of sodium hydrogencarbonate. The resulting ether layer was dried with anhydrous magnesium sulfate, and the solvent was distilled under reduced pressure to give 19.5 g of 1-(4-(tetrahydro-2-pyranyloxy)phenyl)ethanol (yield: 88%).

chloroethyl butyrate was conducted as mentioned below.

To 120 ml of anhydrous diethyl ether was added 22.2 g (0.1 mole) of 1-(4-(tetrahydro-2-pyranyloxy)phenyl)ethanol, 22.4 g (0.1 mole) of 2,2,2-trichloroethyl butyrate and 25.2 g of Lipase P, and the mixture was reacted with stirring at 25° C. for 90 hours. After the reaction mixture was filtered by suction to remove Lipase P, the filtrate was concentrated, and the concentrate was then purified by silica gel chromatography [ethyl acetate/n-hexane=1/4 by volume] to give 10.2 g of S-form of 1-(4-(tetrahydro-2-pyranyloxy)phenyl)ethanol (yield: 92%) and 13.1 g of R-form of 1-(4-(tetrahydro-2-pyranyloxy)phenyl)ethyl butyrate (yield: 91%).

As to the obtained each product, the results of $^1$H-NMR spectrum and the specific rotation, $[α]_D^{20}$ are shown as follows:

S-form of 1-(4-(tetrahydro-2-pyranyloxy)phenyl)ethanol $^1$H-NMR [300NMHz, CDCl$_3$, δ value (ppm)]1.46 (d, 3H), 1.63 (m, 3H), 1.84 (m, 2H), 1.97 (m, 1H), 3.68 (m, 1H), 3.89 (m, 1H), 4.83 (q, 1H), 5.39 (t, 1H), 7.02 (d, 2H), 7.27 (d, 2H)

$[α]_D^{20} = -33.6°$ (CHCl$_3$, c=1)

R-form of 1-(4-(tetrahydro-2-pyranyloxy)phenyl)ethyl butyrate $^1$H-NMR [300MHz, CDCl$_3$, δ value (ppm)]0.90 (t, 3H), 1.19 (t, 3H), 1.47 (d, 3H), 1.49 (d, 3H), 1.62 (m, 2H), 2.27 (t, 2H), 3.51 (m, 1H), 3.76 (m, 1H), 5.35 (q, 1H), 5.84 (q, 1H), 6.94 (d, 2H), 7.26 (d, 2H)

$[α]_D^{20} = +34.1°$ (CHCl$_3$, c=1)

(ii) The transesterification with vinyl valerate was conducted as mentioned below.

The procedure of Example 5 (i) was repeated except that vinyl valerate was used instead of 2,2,2-trichloroethyl butyrate to give 10.4 g of S-form of 1-(4-(tetrahydro-2-pyranyloxy)phenyl)ethanol (yield: 94%) and 13.9 g of R-form of 1-(4-tetrahydro-2-pyranyloxy)phenyl)ethyl valerate (yield: 91%).

As to the obtained each compound, the results of $^1$H-NMR spectrum analysis and the specific rotation, $[\alpha]_D^{20}$ are shown as follows:

As to the S-form of 1-(4-(tetrahydro-2-pyranyloxy)-phenyl ethanol, the same results as those of the S-form obtained in Example 5 (i) were obtained in $^1$H-NMR spectrum analysis.

$[\alpha]_D^{20} = +34.1°$ (CHCl$_3$, c=1)

R-form of 1-(4-(tetrahydro-2-pyranyloxy)phenyl)ethyl valerate $^1$H-NMR [300MHz, CDCl$_3$, δ value (ppm)]0.89 (t, 3H), 1.48 (d, 3H), 1.62 (m, 7H), 1.83 (m, 2H), 1.98 (m, 1H), 2.24 (t, 2H), 3.58 (m, 1H), 3.88 (m, 1H), 5.39 (t, 1H), 5.84 (q, 1H), 7.00 (d, 2H), 7.27 (d, 2H)

$[\alpha]_D^{20} = +77.4°$ (CHCl$_3$, c=1)

EXAMPLE 6

(i) S-form of 1-(4-(tetrahydro-2-pyranyloxy)phenyl)ethyl butyrate was prepared as mentioned below.

In 50 ml of pyridine was dissolved 0.05 mole of the S-form of 1-(4-(tetrahydro-2-pyranyloxy)phenyl)ethyl obtained in Example 5, and 0.06 mole of butyryl chloride was gradually added dropwise to the mixture. After finishing the addition, the reaction was further continued for 10 hours, and the reaction mixture was concentrated under reduced pressure. To the residue was added 100 ml of diethyl ether, and it was washed with diluted hydrochloric acid, water and 10% aqueous solution of sodium hydrogencarbonate. The resulting ether layer was dried with anhydrous magnesium sulfate, and ether was distilled under reduced pressure to give S-form of 1-(4-(tetrahydro-2-pyranyloxy)phenyl)ethyl butyrate (yield: 90%).

As to the obtained compound, the results of $^1$H-NMR spectrum analysis and the specific rotation, $[\alpha]_D^{20}$ are shown as follows:

S-form of 1-(4-(tetrahydro-2-pyranyloxy)phenyl)ethyl butyrate $^1$H-NMR [300MHz, CDCl$_3$, δ value (ppm)]0.89 (t, 3H), 1.48 (d, 3H), 1.62 (m, 5H), 1.83 (m, 2H), 1.98 (m, 1H), 2.24 (t, 2H), 3.58 (m, 1H), 3.88 (m, 1H), 5.39 (t, 1H), 5.84 (q, 1H), 7.00 (d, 2H), 7.27 (d, 2H)

$[\alpha]_D^{20} = -80.6°$ (CHCl$_3$, c=1)

(ii) S-form of 1-(4-hydroxyphenyl)ethyl butyrate was prepared as mentioned below.

In 150 ml of methanol was dissolved 0.1 mole of the S-form of 1-(4-(tetrahydro-2-pyranyloxy)phenyl)ethyl butyrate, 1.1 g of pyridinium p-toluenesulfonate was added thereto, and the mixture was subjected to reaction at room temperature for 2 hours. Then, methanol was distilled under reduced pressure, to which 200 ml of ether was added, and the mixture was washed with water. The resulting ether layer was dried with anhydrous magnesium sulfate, and ether was distilled under reduced pressure to give S-form of 1-(4-hydroxyphenyl)ethyl butyrate (yield: 13%).

As to the obtained compound, the same results as those of the compound obtained in Example 3 (ii) were obtained in $^1$H-NMR spectrum analysis.

Also, the result of the specific rotation, $[\alpha]_D^{20}$ is $-109.8°$, (CHCl$_3$, c=1)

(iii) R-form of 1-(4-hydroxyphenyl)ethyl butyrate was prepared as mentioned below.

In 150 ml of methanol was dissolved 0.1 mole of the R-form of 1-(4-(tetrahydro-2-pyranyloxy)phenyl)ethyl butyrate, to which 1.1 g of pyridinum, p-toluenesulfonate, and the mixture was subjected to reaction at room temperature for 2 hours. Then, methanol was distilled under reduced pressure, 200 ml of ether was added thereto, and it was washed with water. The resulting ether layer was dried with anhydrous magnesium sulfate, and ether was distilled under reduced pressure to give R-form of 1-(4-hydroxyphenyl)ethyl butyrate (yield: 11%).

As to the obtained compound, the same results as those of the compound obtained in Example 3 (iii) were obtained in $^1$H-NMR spectrum analysis.

$[\alpha]_D^{20} = 110.1°$, (CHCl$_3$, c=1)

(iv) R-form of 1-(4-hydroxyphenylethyl)valerate was prepared as mentioned below.

The procedure of Example 3 (iii) was repeated except that 1-(4-(tetrahydro-2-pyranyloxy)phenyl)ethyl valerate was used instead of 1-(4-(tetrahydro-2-pyranyloxy)-phenyl)ethyl butyrate to give R-form of 1-(4-hydroxyphenyl)ethyl valerate (yield: 10%).

As to the obtained compound, the same results as those of the compound obtained in Example 3 (iii) were obtained in $^1$H-NMR spectrum analysis.

$[\alpha]_D^{20} = -83.5°$, (CHCl$_3$, c=1)

The optically active compounds are utilized for easily preparing additives (chiral dopants) optically active which are excellent in compatibility with the known smectic liquid crystals or nematic liquid crystals and are capable of producing liquid crystal compounds having high Ps value. The optically active compounds can be easily prepared according to the process of the invention, as shown above.

EXAMPLE 7

[Preparation of S-form of 4'-{1''-(decanoyloxy)ethyl}-phenyl-2-(p-octyloxyphenyl)pyrimidine-5-carboxylate]

(i) p-Octyloxybenzonitrile was prepared as mentioned below.

In 4000 ml of acetone was dissolved 500 g (4.2 moles) of p-hydroxybenzonitrile and 965 g (5.0 moles) of octyl bromide, 828 g (6.0 moles) of anhydrous potassium carbonate was added thereto, and the mixture was refluxed with heating for 30 hours. Then, the inorganic salt was filtered off from the reaction mixture, acetone was distilled under reduced pressure. To the residue was added 2000 ml of ether and the mixture was washed with 2N aqueous solution of sodium hydroxide, water, then saturated aqueous solution of sodium chloride. The resulting organic layer was dried with anhydrous magnesium sulfate, and ether was distilled under reduced pressure to give 855 g of p-octyloxybenzonitrile (yield: 88%).

As to the obtained compound, the results of $^1$H-NMR spectrum analysis are shown as follows:

$^1$H-NMR [300MHz, CDCl$_3$, δ value (ppm)]0.86 (t, 3H), 1.26 (m, 10H), 1.42 (m, 2H), 1.77 (m, 2H), 3.96 (t, 2H), 6.90 (d, 2H), 7.55 (d, 2H)

(ii) Ethyl 2-(p-octyloxyphenyl)pyrimidine-5-carboxylate was prepared as mentioned below.

In a mixed solvent of 120 ml of anhydrous ethanol and 160 ml of anhydrous benzene was dissolved 170 g (0.74 mole) of p-octyloxybenzonitrile, through which hydrogen chloride gas was passed at 0° C. with cooling to saturate. The reaction was continued at room temperature for 15 hours with stirring. The solvent was distilled under reduced pressure, to the residue was added 300 ml of diethyl ether. The precipitate was filtered off and was dried to give 150 g of a crude p-octyloxyphenylimide ethyl ether hydrochloride (yield: 65%).

Into 800 ml of anhydrous ethanol was dispersed 150 g of the obtained imide ethyl ether hydrochloride, through which ammonium gas was passed to dissolve, and the mixture was subjected to reaction at room temperature for 40 hours with stirring. Ethanol was distilled under reduced pressure, and to the residue was added 500 ml of diethyl ether to precipitate. The precipitate was filtered off and was dried to give 101 g of p-octyloxyphenylamidine.hydrochloride (yield: 74%).

In anhydrous ethanol was dissolved 100 g (0.37 mole) of the obtained p-octyloxyphenylamidine. hydrochloride and 14.6 g (0.37 mole) of diethyl ethoxyethylene malonate, to which 7.6 g (0.74 mole) of sodium ethoxide was added, and the mixture was refluxed with heating for 8 hours. Then, the obtained yellow reaction mixture was concentrated under reduced pressure, to the concentrate was added 500 ml of cool water, and it was adjusted with acetic acid to a pH of 3. After filtering, the precipitate was thoroughly washed with water and was recrystallized from THF to give 90 g of ethyl 2-(p-octyloxyphenyl)-4-hydroxypyrimidine-5-carboxylate (yield: 65%).

Then, 5 g (0.013 mole) of the obtained ethyl 2-(p-octyloxyphenyl)-4-hydroxypyrimidine-5-carboxylate was dissolved in 25 ml of phosphorus oxychloride, and the mixture was refluxed with heating for 3 hours. The excess phosphorus oxychloride was distilled under reduced pressure, and the residue was purified by silica gel chromatography (developing solvent: CHCl$_3$) to give 4.9 g of ethyl 2-(p-octyloxyphenyl)-4-chloropyrimidine-5-carboxylate (yield: 91%).

Then, 4.9 g (0.012 mole) of the obtained 2-(p-octyloxyphenyl)-4-chloropyrimidine-5-carboxylate was dissolved in 100 ml of ethanol, and was reduced with 0.3 g of Pd/BaSO$_4$ in the presence of potassium acetate to give 4.0 g of ethyl 2-(p-octyloxyphenyl)pyrimidine-5-carboxylate (yield: 93%).

As to the obtained compound, the results of $^1$H-NMR spectrum analysis are as follows:

$^1$H-NMR [300MHz, CDCl$_3$, δ value (ppm)]0.84 (t, 3H), 1.28 (m, 10H), 1.47 (t, 3H), 1.78 (m, 2H), 4.00 (t, 2H), 4.41 (q, 2H), 6.96 (d, 2H), 8.42 (d, 2H), 9.22 (s, 2H)

(iii) S-form of 4'-(1''-(decanoyloxy)ethyl)phenyl-2-(p-octyloxyphenyl)pyrimidine-5-carboxylate was prepared as mentioned below.

There was refluxed with heating for 5 hours 4.0 g (0.011 mole) of ethyl 2-(p-octyloxyphenyl)pyrimidine-5-carboxylate in a solution of 1.1 equivalents of potassium hydroxide dissolved in 80% aqueous solution of ethanol to hydrolyze.

In 20 ml of methylene chloride was dissolved 2.9 g (0.009 mole) of the obtained 2-(p-octyloxyphenyl)-pyrimidine)-5-carboxylic acid and 2.6 g (0.009 mole) of the S-form of decanoic acid ester of 1-(p-hydroxyphenyl)ethanol, to which 1.8 g (0.009 mole) of dichlorohexyl carbodiimide and 0.9 g (0.009 mole) of triethyl amine were added, and the mixture was subjected to reaction for hours. The reaction mixture was concentrated under reduced pressure, to the concentrate was added 50 ml of chlcroform, and it was washed with 0.1 N aqueous solution of hydrochloric acid, water, 0.1 N aqueous solution of potassium hydroxide, and then water. The resulting organic layer was dried with anhydrous magnesium sulfate, concentrated and purified by silica gel chromatography (developing solvent: chloroform) to give 3.8 g of S-form of 4'-(1''-(decanoyloxy)ethyl)phenyl-2-(p-octyloxyphenyl)-pyrimidine-5-carboxylate (yield: 71%).

As to the obtained compound, the results of $^1$H-NMR spectrum analysis, FT-IR spectrum analysis, the specific rotation and the clear point are shown as follows:

$[\alpha]_D^{20}= -34.5°$, (CHCl$_3$, c=1)

Clear point: 98.9° C.

$^1$H-NMR[300MHz, CDCl$_3$, δ value (ppm)]0.86 (m, 6H), 1.25 (m, 20H), 1.47 (m, 2H), 1.53 (d, 3H), 1.62 (m, 2H), 1.81 (m, 2H), 2.31 (t, 2H), 4.04 (t, 2H), 5.91 (q, 1H), 7.00 (d, 2H), 7.21 (d, 2H), 7.42 (d, 2H), 8.49 (d, 2H), 9.36 (d, 2H)

FT-IR (cm$^{-1}$) 3039, 2954, 2924, 2870, 2854, 1739, 1697, 1589, 1543, 1508, 1465, 1438, 1388, 1377, 1334, 1288, 1257, 1242, 1199, 1168, 1103, 1057, 1010, 976, 964, 941, 910, 888, 852, 802, 771, 748, 721, 651, 555, 528, 497, 486, 451

EXAMPLE 8

[Preparation of S-form of 4'-(1''-(heptanoyloxy)ethyl)phenyl-2-(p-octyloxyphenyl)pyrimidine-5-carboxylate]

The procedure of Example 7 (iii) was repeated except that the S-form of 1-(p-hydroxyphenyl)ethyl heptanoate was used instead of 1-(p-hydroxyphenyl)ethyl decanoate to give 3.4 g of 4'-(1''-(heptanoyloxy)ethyl)phenyl-2-(p-octyloxyphenyl)pyrimidine-5-carboxylate (yield: 68%).

As to the obtained compound, the results of 1H-NMR spectrum analysis, FT-IR spectrum analysis, the specific rotation, $[\alpha]_D^{20}$ and the clear point are shown as follows:

$[\alpha]_D^{20}= -37.0°$ (CHCl$_3$, c=1)

Clear point: 103.9° C.

$^1$H-NMR [300MHz, CDC:3, δ value (ppm)]0.86 (m, 6H), 1.25 (m, 14H), 1.47 (m, 2H), 1.53 (d, 3H), 1.62 (m, 2H), 1.81 (m, 2H), 2.31 (t, 2H), 4.04 (t, 2H), 5.91 (q, 1H), 7.00 (d, 2H), 7.21 (d, 2H), 7.42 (d, 2H), 8.49 (d, 2H), 9.36 (d, 2H)

FT-IR (cm$^{-1}$) 3039, 2954, 2927, 2873, 2854, 1739, 1697, 1589, 1543, 1508, 1465, 1438, 1388, 1377, 1334, 1288, 1257, 1238, 1199, 1168, 1103, 1057, 1018, 976, 937, 914, 883, 852, 771, 748, 725, 651, 555, 532

EXAMPLE 9

Preparation of S-form of 4'-(1''-(butanoyloxy)ethyl)phenyl-2-(p-octyloxyphenyl)pyrimidine-5-carboxylate]

The procedure of Example 7 (iii) was repeated except that the S-form of butanoic acid ester of 1-(p-hydroxyphenyl)ethanol obtained in Example 3 (ii) was used instead of the S-form of 1-(p-hydroxyphenyl)ethyl decancate to give 3.2 g of S-form of 4'-(1''-(butanoyloxy)ethyl)phenyl-2-(p-octyloxyphenyl)pyrimidine-5-cartoxylate (yield: 66%).

As to the obtained compound, the results of $^1$H-NMR spectrum analysis, FT-IR spectrum analysis, the specific rotation, $[\alpha]_D^{20}$ and the clear point are shown as follows:

$[\alpha]_D^{20}= -40.3°$, (CHCl$_3$, c=1)

Clear point: 107.8° C.

¹H-NMR [300MHz, CDCl₃, δ value (ppm)]0.89 (m, 6H), 1.35 (m, 8H), 1.50 (m, 2H), 1.55 (d, 3H), 1.70 (m, 2H), 1.82 (m, 2H), 2.32 (t, 2H), 4.10 (t, 2H), 5.91 (q, 1H), 6.99 (d, 2H), 7.20 (d, 2H), 7.42 (d, 2H), 8.49 (d, 2H), 9.37 (d, 2H)

FT-IR (cm⁻¹) 3040, 2954, 2927, 2873, 2856, 1739, 1697, 1589, 1543, 1508, 1466, 1438, 1390, 1377, 1335, 1288, 1257, 1238, 1200, 1168, 1105, 1057, 1018, 978, 937, 914, 883, 853, 773, 748, 727, 651, 555, 534

EXAMPLE 10

Preparation of R-form of 4'-(1''-(decanoyloxy)ethyl)phenyl-2-(p-octyloxyphenyl)pyrimidine-5-carboxylate]

The procedure of Example 7 (iii) was repeated except that the R-form of 1-(p-hydroxyphenyl)ethyl decanoate obtained in Example 3 (iv) was used instead of the S-form of 1-(p-hydroxyphenyl)ethyl decanoate to give 3.7 g of R-form of 4'-(1''-(decanoyloxy)ethyl)phenyl-2-(p-octyloxyphenyl)pyrimidine-5-carboxylate (yield: 68%).

As to the obtained compound, the results of the specific rotation and the clear point are shown as follows:

$[\alpha]_D^{20} = +34.5°$, (CHCl₃, c=1)

Clear point: 98.9° C.

As to ¹H-NMR spectrum analysis and FT-IR spectrum analysis, the same results as those of the compound obtained in Example 7 (iii) were obtained.

EXAMPLE 11

[Preparation of R-form of 4'-(1''-(heptanoyloxy)ethyl)phenyl-2-(p-octyloxyphenyl)pyrimidine-5-carboxylate]

The procedure of Example 7 (iii) was repeated except that the R-form of 1-(p-hydroxyphenyl)ethyl heptanoate obtained in Example 3 (iv) was used instead of S-form of 1-(p-hydroxyphenyl)ethyl decanoate to give 3.5 g of R-form of 4'-(1,'-(heptanoyloxy)ethyl)phenyl-2-(p-octyloxyphenyl)pyrimidine-5-carboxylate (yield: 70%).

As to the obtained compound, the results of the specific rotation and the clear point are shown in as follows:

$[\alpha]_D^{20} = +37.8°$, (CHCl₃, c=1)

Clear point: 103.9° C.

As to ¹H-NMR spectrum analysis and FT-IR spectrum analysis, the same results as those of the compound obtained in Example 8 were obtained.

EXAMPLE 12

[Preparation of R-form of 4'-(1''-(butanoyloxy)ethyl)phenyl-2-(p-octyloxyphenyl)pyrimidine-5-carboxylate]

The procedure of Example 7 (iii) was repeated except that the R-form of 1-(p-hydroxyphenyl)ethyl butanoate obtained in Example 3 (iv) was used instead of the S-form of 1-(p-hydroxyphenyl)ethyl decanoate to give 3.0 g of R-form of 4'-(1''-(butanoyloxy)ethyl)phenyl-2-(p-octyloxyphenyl)pyrimidine-5-carboxylate (yield: 65%).

As to the obtained compound, the results of the specific rotation and the clear point are shown in as follows:

$[\alpha]_D^{20} = +41.1°$, (CHCl₃, c=1)

Clear point: 107.8° C.

As to ¹H-NMR spectrum analysis and FT-IR spectrum analysis, the same results as those of the compound obtained in Example 9 were obtained.

EXAMPLE 13

[Preparation of S-form of 4''-(1'''-(decanoyloxy)ethyl)phenyl-4-(trans-2'-(5'-heptyl)-1',3'-dioxanyl)benzoate]

(i) 2-heptyl-1,3-propanediol was prepared as mentioned below.

To 400 ml of anhydrous ethanol was added 18.4 g (0.8 mole) of sodium metal and 128 g (0.8 mole) of diethyl malonate, then 143.1 g (0.8 mole) of heptane bromide was added thereto, and the mixture was refluxed with heating for 8 hours. Then, ethanol was distilled under reduced pressure, to the residue was added 500 ml of diethyl ether and it was washed with water, dried with anhydrous magnesium sulfate and was concentrated under reduced pressure.

In anhydrous diethyl ether was dissolved 100 g of the obtained diethyl heptylmalonate, and the mixture was added dropwise to a solution of 28.7 g of lithium aluminum hydride dispersed in 270 ml of diethyl ether. The mixture was stirred for 15 hours. Then, to the reaction mixture was added gradually 3N hydrochloric acid to make excess lithium aluminum hydride inactive. After washing with 10% aqueous solution of sodium carbonate, then water, the resulting ether layer dried with anhydrous magnesium sulfate. After distilling ether under reduced pressure, the residue was purified by silica gel chromatography (developing solvent: hexane/ethyl acetate=4/1) and distilled under reduced pressure to give 41.2 of 2-heptyl-1,3-propanediol (yield: 6%).

As to the obtained compound, the results of ¹H-NMR spectrum analysis are shown as follows:

¹H-NMR [300 MHz, CDCl₃, δ value (ppm)]: 0.83 (t, 3H), 1.22 (br.s, 12H), 1.73 (m, 1H), 2.88 (br.s. 2H), 3.60 (m, 2H), 3.76 (m, 2H)

(ii) Trans-2-(p-methoxycarbonylphenyl)-5-heptyl-1,3-dioxane was prepared as mentioned below.

In 100 ml of benzene was dissolved 19 g (0.11 mole) of 2-heptyl-1,3-propandiol, 18 g (0.11 mole) of methyl ester of terephthalaldehydric acid and 0.07 g (0.0003 mole) of sulfosalicylic acid and the mixture was refluxed for 24 hours and dehydrated. After cooling the reaction mixture to room temperature, the residue was washed with 0.1 N aqueous solution of sodium hydroxide and water, and the organic layer was dried with anhydrous magnesium sulfate. Then, the organic layer was distilled under reduced pressure, and the residue was recrystallized from ethanol, filtered and dried to give 14.5 g of trans-2-(p-methoxycarbonylphenyl)-5-heptyl-1,3-dioxane (yield: 41%).

As to the obtained compound, the results of ¹H-NMR spectrum analysis are shown as follows:

¹H-NMR [300 MHz, CDCl₃, δ value (ppm)]: 0.86 (t, 3H), 1.08 (m, 2H), 1.26 (br.s, 10H), 2.11 (m, 1H), 3.52 (t, 2H), 3.88 (s, 3H), 4.23 (m, 2H), 5.41 (s, 1H), 7.53 (d, 2H), 8.02 (d, 2H)

(iii) S-form of 4''-(1'''-(decanoyloxy)ethyl)phenyl-4-(trans-2'-(5'-heptyl)-1',3'-dioxanyl) benzoate was prepared as mentioned below.

In methanol was dissolved 5 g (0.016 mole) of trans-2-(p-methoxycarbonylphenyl)-5-heptyl-1,3-dioxane, to which 1.2 equivalents of potassium hydroxide was added, and the mixture was refluxed for 8 hours with heating. After distilling methanol under reduced pressure, 300 ml of ethyl acetate was added to the residue, and the mixture was neutralized with 10% aqueous solution of hydrochloric acid while cooling at a temperature of −10° C. Then, the organic layer was concentrated and was recrystallized from methanol to give 4.2 g of trans-2-(p-hydroxycarbonylphenyl)-5-heptyl-1,3-dioxane (yield: 86%).

Then, 3 g (0.01 mole) of the obtained trans-2-(p-hydroxycarbonylphenyl)-5-heptyl-1,3-dioxane, 1.0 g of triethyl amine and 0.8 g of pyridine were dissolved in 150 m± of methylene chloride, to which 1.4 g (0.01 mole) of isobutyl chloroformate was added, and the mixture was stirred for 5 hours. Further, a solution of 2.9 g (0.01 mol) of the S-form of 1-(p-hydroxyphenyl)ethyl decanoate dissolved in methylene chloride was added to the resulting mixture, and the mixture was subjected to reaction with stirring at room temperature for 20 hours. The reaction mixture was concentrated under reduced pressure and purified by silica gel chromatography (developing solvent: CHCl$_3$) to give 3.3 g of S-form of 4″-(1‴-(decanoyloxy)ethyl)phenyl-4-(trans-2′-(5′-heptyl-1′,3′-dioxanyl)benzoate (yield: 62 The obtained compound was in crystalline state.

As to the obtained compound, the results of $^1$H-NMR spectrum analysis, FT-IR spectrum analysis, the specific rotation, $[\alpha]_D^{20}$ and the clear point are shown as follows:

$[\alpha]_D^{20} = -32.8°$, (c=1, CHCl$_3$)

Clear point: 60.9° C. $^1$H-NMR [300 MHz, CDCl$_3$ δ value (ppm)]: 0.86 (m, 6H), 1.11 (m, 2H), 1.27 (m, 22H), 1.52 (d, 3H), 1.60 (m, 2H), 2.12 (m, 1H), 2.30 (t, 2H), 3.51 (t, 2H), 4.25 (m, 2H), 5.46 (s, 1H), 5.90 (q, 1H), 7.18 (d, 2H), 7.39 (d, 2H), 7.61 (d, 2H), 8.17 (d, 2H)

FT-IR(cm$^{-1}$): 2958, 2924, 2850, 1739, 1724, 1612, 1512, 1465, 1415, 1384, 1342, 1334, 1288, 1269, 1238, 1215, 1184, 1172, 1141, 1130, 1084, 1057, 1016, 995, 976, 956, 941, 895, 871, 841, 817, 775, 756, 721, 705, 698, 655, 590, 551

EXAMPLE 14

[Preparation of S-form of 4″-(1‴-(heptanoyloxy)ethyl)phenyl-4-(trans-2′-(5′-heptyl)-1′,3′-dioxanyl) benzoate]

The procedure of Example 13 (iii) was repeated except that the S-form of 1-(p-hydroxyphenyl)ethyl heptanoate obtained in Example 3 (ii) was used instead of the S-form of 1-(p-hydroxyphenyl)ethyl decanocate to give 3.7 g of S-form of 4″-(1‴-(heptanoyloxy)ethyl)-phenyl-4-trans-2′-(5′-heptyl)-1′,3′-dioxanyl)benzoate (yield: 68%).

As to the obtained compound, the results of $^1$H-NMR spectrum analysis, FT-IR spectrum analysis, the specific rotation and the clear point are shown in as follows:

$[\alpha]_D^{20} = -39.5°$, (CHCl$_3$, c=1)

Clear point: 71.3° C.

$^1$H-NMR [300 MHz, CDC:3 δ value (ppm)]: 0.86 (t, 6H), 1.11 (m, 2H), 1.27 (br.s, 16H), 1.52 (d, 3H), 1.61 (m, 2H), 2.12 (m, 1H), 2.31 (t, 2H), 3.54 (t, 2H), 4.24 (m, 2H), 5.46 (s, 1H) 5.90 (q, 1H), 7.18 (d, 2H), 7.39 (d, 2H), 7.61 (d, 2H), 8.17 (d, 2H)

FT-IR(cm$^{-1}$) 2958, 2924, 2854, 1739, 1724, 1612, 1512, 1465, 1415, 1384, 1346, 1334, 1292, 1273, 1238, 1219, 1208, 1188, 1172, 1130, 1084, 1060, 1018, 995, 976, 956, 895, 871, 841, 756, 725, 705, 690, 655, 590, 547

EXAMPLE 15

[Preparation of S-form of 4″-(1‴-(butanoyloxy)ethyl)phenyl-4-(trans-2′-(5′-heptyl)-1′,3′-dioxanyl)benzoate]

The procedure of Example 13 (iii) was repeated except that the S-form of 1-(p-hydroxyphenyl)ethyl butancate obtained in Example 3 (ii) was used instead of the S-form of 1-(p-hydroxyphenyl)ethyl decanoate to give 3.4 g of S-form of 4″-(1‴-(butanoyloxy)ethyl)phenyl-4-(trans-2′-(5′-heptyl)-1′,3′-dioxanyl)benzoate (yield: 69%).

As to the obtained compound, the results of 1H-NMR spectrum analysis, FI-IR spectrum analysis, the specific rotation and the clear point are shown in as follows:

$[\alpha]_D^{20} = -46.5°$, (CHCl$_3$, c=1)

Clear point: 80.9° C.

$^1$H-NMR [300 MHz, CDCl$_3$ δ value (ppm)]: 0.91 (m, 6H), 1.13 (m, 2H), 1.29 (m, 10H), 1.53 (d, 3H), 1.65 (m, 2H), 2.21 (m, 1H), 2.34 (t, 2H), 3.70 (t, 2H), 4.23 (m, 2H), 5.48 (s, 1H) 5.90 (q, 1H), 7.18 (d, 2H), 7.39 (d, 2H), 7.61 (d, 2H), 8.17 (d, 2H)

FT-IR(cm$^{-1}$): 2960, 2926, 2856, 1739, 1724, 1612, 1512, 1465, 1415, 1384, 1346, 1334, 1292, 1273, 1240, 1219, 1208, 1190, 1172, 1130, 1086, 1060, 1018, 995, 976, 956, 895, 871, 843, 756, 725, 708, 690, 657, 590, 548

EXAMPLE 16

[Preparation of R-form of 4″-1‴-(decanoyloxy)ethyl)phenyl-4-(trans-2′-(5′-heptyl)-1′,3′-dioxanyl)benzoate]

The procedure of Example 13 (iii) was repeated except that the R-form of 1-(p-hydroxyphenyl)ethyl decanoate obtained in Example 3 (iv) was used instead of the S-form of 1-(p-hydroxyphenyl)ethyl decanoate to give 3.9 g of R-form of 4″-(1‴-(decanoyloxy)ethyl)phenyl-4-(trans-2′-(5′-heptyl)-1′,3′-dioxanyl)benzoate (yield: 67%).

As to the obtained compound, the results of the phase transition temperature, the specific rotation and the clear point are shown as follows: Phase transition temperature (measured by polarizing microscope equipped with a hot stage):

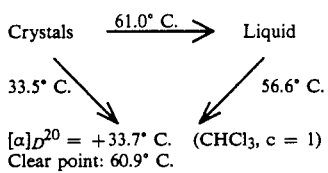

$[\alpha]_D^{20} = +33.7°$ C. (CHCl$_3$, c = 1)
Clear point: 60.9° C.

As to $^1$H-NMR spectrum analysis and FT-IR spectrum analysis, the same results as those of the compound obtained in Example 13 (iii) were obtained.

EXAMPLE 17

[Preparation of R-form of 4″-(1‴-(heptanoyloxy)ethyl)phenyl-4-(trans-2′-(5′-heptyl)-1′,3′-dioxanyl)benzoate]

The procedure of Example 13 (iii) was repeated except that the R-form of 1-(p-hydroxyphenyl)ethyl heptanoate obtained in Example 3 (iv) was used instead of the S-form of 1-(p-hydroxyphenyl)ethyl decanoate to give 3.8 g of R-form of 4″-(1‴-(heptanoyloxy)ethyl)-phenyl-4-(trans-2′-(5′-heptyl)-1′,3′-dioxanyl)benzoate (yield: 70%).

As to the obtained compound, the results the phase transition temperature, of the specific rotation and the clear point are shown in as follows:

$[\alpha]_D^{20} = +40.4°$, (CHCl$_3$, c=1)

Clear point: 71.3° C.

As to $^1$H-NMR and FT-IR spectrum, the same results as those of the compound obtained in Example 14 were obtained.

EXAMPLE 18

[Preparation of R-form of 4''-(1'''-(butanoyloxy)ethyl)phenyl-4-(trans-2'-(5'-heptyl)-1',3'-dioxanyl)benzoate]

The procedure of Example 13 (iii) was repeated except that the R-form of 1-(p-hydroxyphenyl)ethyl butanoate obtained in Example 3 (iv) was used instead of the S-form of 1-(p-hydroxyphenyl)ethyl decanoate to give 3.3 g of R-form of 4''-(1'''-(butanoyloxy)ethyl)phenyl-4-(trans-2'-(5'-heptyl)-1',3'-dioxanyl)benzoate (yield: 66 %.

As to the obtained compound, the results of the specific rotation, $[\alpha]_D^{20}$ and the clear point are shown as follows:

$[\alpha]_D^{20} = +47.5°$, (CHCl$_3$, c=1)

Clear point: 80.9° C.

As to $^1$H-NMR spectrum analysis and FT-IR spectrum analysis, the same results as those of the compound obtained in Example 15 were obtained.

The optically active compounds are useful as additives to be added to ferroelectric liquid crystal compounds, and the compounds can be easily prepared according to the process of the present invention, as shown above.

In addition to the ingredients used in the Examples, other ingredients can be used in the Examples as set forth in the specification to obtain substantially the same results.

What is claimed is:

1. An optically active compound of the formula

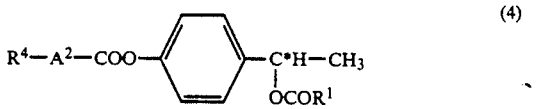

wherein R$^1$ is an alkyl group having 1 to 15 carbon atoms, R$^4$ is an alkyl or alkyloxy group having 1 to 15 carbon atoms and A$^2$ is

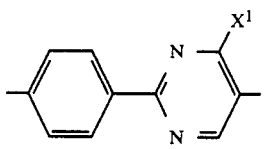

in which X$^1$ is hydrogen atom, a halogen atom or cyano group.

* * * * *

UNITED STATES PATENT AND TRADEMARK OFFICE
CERTIFICATE OF CORRECTION

PATENT NO. : 5,053,507

DATED : October 1, 1991

INVENTOR(S) : Moriuchi et al

It is certified that error appears in the above-identified patent and that said Letters Patent is hereby corrected as shown below:

On the cover page, Item [54], "OPTICALLY ACTIVE PYRIMIDINES DERIVATIVES" should read --OPTICALLY ACTIVE COMPOUND AND PROCESS FOR PREPARING THE SAME--.

Signed and Sealed this

Eighth Day of February, 1994

Attest:

BRUCE LEHMAN

Attesting Officer

Commissioner of Patents and Trademarks